United States Patent [19]

Sutter

[11] Patent Number: 4,732,149
[45] Date of Patent: Mar. 22, 1988

[54] BIPOLAR MEDICAL COAGULATION INSTRUMENT

[76] Inventor: Hermann Sutter, Steinmatten 28, D-7803 Gundelfingen, Fed. Rep. of Germany

[21] Appl. No.: 8,043

[22] Filed: Jan. 21, 1987

Related U.S. Application Data

[63] Continuation of Ser. No. 820,958, Jan. 21, 1986, abandoned.

[30] Foreign Application Priority Data

Jan. 22, 1985 [DE] Fed. Rep. of Germany ....... 3501863

[51] Int. Cl.[4] .............................................. A61B 17/39
[52] U.S. Cl. ................. 128/303.17; 219/234
[58] Field of Search ...................... 128/303.13, 303.14, 128/303.17, 303.19, 321, 354; 219/234, 240

[56] References Cited

U.S. PATENT DOCUMENTS

| 1,071,978 | 9/1913 | White | 128/303.13 |
| 1,945,327 | 1/1934 | Morse | 128/303.17 |
| 3,322,124 | 5/1967 | Ireland | 219/234 X |
| 3,643,663 | 2/1972 | Sutter | 128/303.17 |
| 3,752,160 | 8/1973 | Billin | 128/303.17 |
| 3,938,527 | 2/1976 | Rioux et al. | 128/303.17 |
| 4,137,919 | 2/1979 | Farin et al. | 128/303.17 |
| 4,461,297 | 7/1984 | Sutter | 128/321 |
| 4,552,143 | 11/1985 | Lottick | 128/303.17 X |

FOREIGN PATENT DOCUMENTS 3012849 4/1982 Fed. Rep. of Germany ........................ 128/303.17

Primary Examiner—Lee S. Cohen
Attorney, Agent, or Firm—Peter K. Kontler

[57] ABSTRACT

The legs of a forceps constitute two coagulation electrodes each of which has a jaw at one end and a terminal at the other end. The two terminals are electrically insulated from each other and constitute a projection having a spherical or frustoconical portion which can be inserted into a socket at the front end of a pistol-shaped coupling device serving to connect the electrodes with a source of high-frequency energy when the forceps is to be used as a coagulation instrument. The terminals of the legs can be moved into mere abutment with the terminals of conductors which are embedded in the insulating carrier of the coupling device. If the terminals of the coagulation electrodes form a projection with a spherical portion and a smaller-diameter cylindrical portion, the coupling device can be caused to swivel with reference to the forceps through angles of up to 40 degrees from a position in which the axis of the conical or frustoconical internal surface bounding the socket coincides with the axis of the cylindrical portion. The absence of the need for a positive connection between the terminals of the coagulation electrodes and the terminals of the conductors renders it possible to abruptly shift from utilization of the forceps as a separate mechanical instrument to utilization of the forceps as a part of a coagulation instrument or vice versa without any changes in the position of the forceps relative to the body of a patient.

23 Claims, 5 Drawing Figures

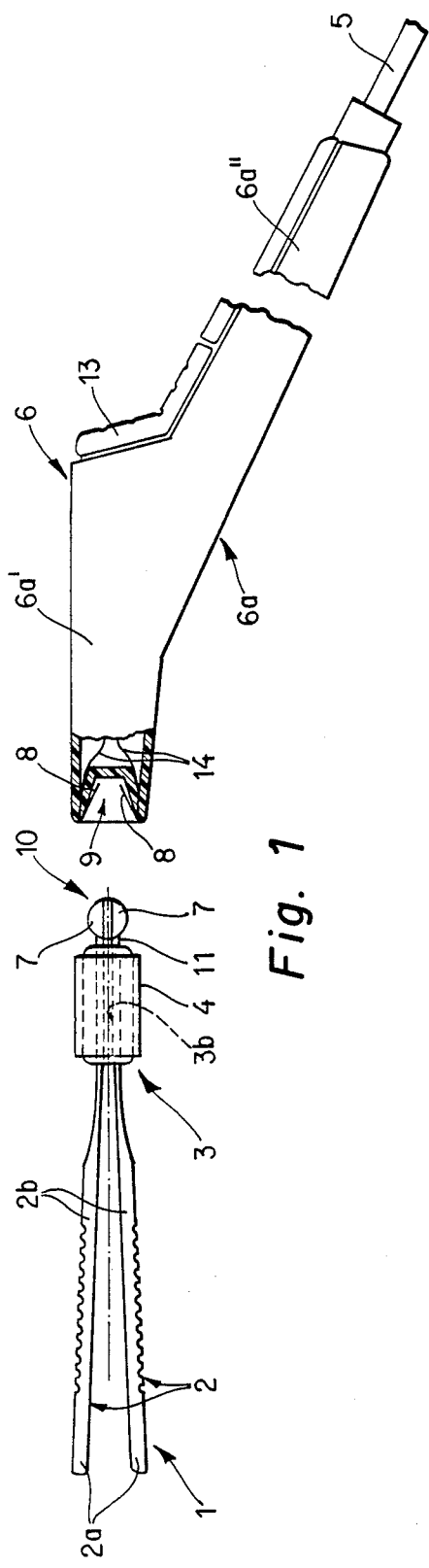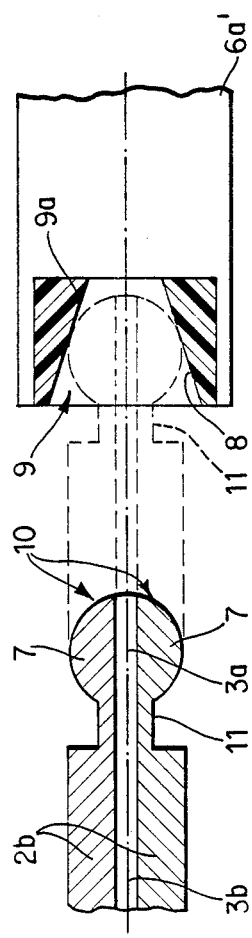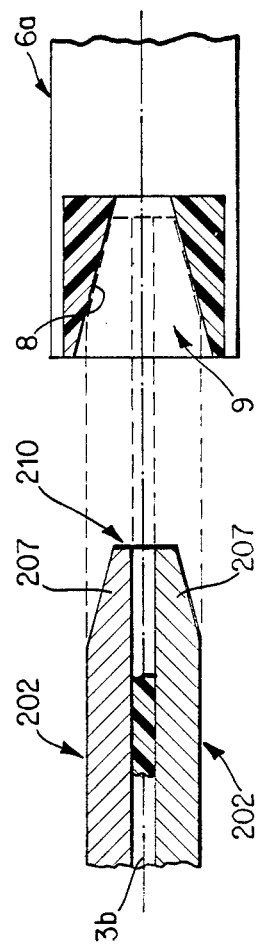

BIPOLAR MEDICAL COAGULATION INSTRUMENT

This application is a continuation, of application Ser. No. 820,958, filed Jan. 21, 1986, now abandoned.

CROSS-REFERENCE TO RELATED CASES

Applicant is the inventor named in the copending patent application Ser. No. 809,055 filed December, 1985 for "Bipolar forceps", now abandoned, and the patentee named in U.S. Pat. No. 4,461,297 granted July 24, 1984 for "Forceps".

BACKGROUND OF THE INVENTION

The present invention relates to improvements in bipolar medical coagulation instruments in general, and more particularly to improvements in instruments of the type wherein the tissue or vessels can be clamped, held and/or otherwise manipulated by the jaws of an implement which resembles or constitutes a forceps (hereinafter called forceps). Still more particularly, the invention relates to improvements in medical instruments of the type wherein the forceps comprises two coagulation electrodes each of which includes a jaw movable toward or away from the other jaw to thereby pinch or release a piece of tissue, a blood vessel or another part of an animal body.

It is already known to construct the jaws of a forceps in such a way that they constitute the electrodes of a bipolar coagulation instrument and to provide on the electrodes means for securing them to conductors leading to a source of high-frequency electrical energy. The jaws constitute two poles of the high-frequency circuit which can contact a piece of tissue or a vessel while the surgeon uses the forceps in the course of a microsurgical or other operation. Reference may be had, for example, to commonly owned German Pat. No. 30 12 849 which discloses a forceps with an insulating carrier for the rear ends of the legs. The legs extend rearwardly beyond the carrier and such portions of the legs constitute terminals which are connectable to the poles of a source of high-frequency electrical energy. As a rule, the connection between the energy source and the forceps comprises a receptacle for insertion of the terminals at the rear end of the forceps whereby the terminals are held in the receptacle by friction or in another more or less positive manner.

Coagulation and termination of bleeding in general surgery and orthopedics (macrosurgery) is normally effected by standard anatomic and surgical forcipes whose jaws are used to grasp and/or otherwise manipulate pieces of tissue or vessels. Such implements cannot be used for bipolar coagulation so that the surgeon is compelled to resort to monopolar coagulation with attendant undesirable results. Thus, monopolar coagulation entails the danger that it can propagate itself deeper from as well as laterally of the neutral electrode which can result in destruction of or lesser damage to the vessels and nerve cords around the locus of coagulation.

Since the work of a surgeon must be completed as rapidly as possible, it is necessary to design the forcipes in such a way that they can be used for grasping of tissue as well as for preparation and (if necessary) monopolar coagulation. Such work is seldom performed by conventional bipolar coagulation forcipes which, as a rule, are not used in general surgery and orthopedics. One of the reasons is that a bipolar coagulation forceps of conventional design must be attached to conductors which connect it with a source of high-frequency electrical energy, and such conductors interfere with manipulation of the forceps in general surgery and/or orthopedics. The surgeon normally employs a conventional forceps to engage a vessel in order to interrupt the bleeding and, in order to terminate the bleeding, the conventional forceps is thereupon replaced by a bipolar coagulation forceps with conductors leading to the energy source. As a rule, the vessel begins to bleed again as soon as it is released by the standard forceps so that the wound is filled with blood before the surgeon can get hold of and apply the bipolar coagulation forceps. The same holds true for conventional surgical clamps which are often used to interrupt the bleeding of vessels prior to the application of a bipolar coagulation forceps.

U.S. Pat. No. 1,071,978 to White discloses a device which serves to remove hairs and wherein the rear ends of the legs of tweezers are connectable to electrical conductors. For this purpose, the rear ends of the legs are formed with eyelets for reception of pin-shaped plugs or terminals which are held in the respective eyelets by friction. A drawback of such proposal is that the insertion of plugs into the eyelets necessitates an interruption of the utilization of tweezers for their primary purpose as well as that the interruption is rather long-lasting which is evidently undesirable in general surgery or orthopedics.

OBJECTS AND SUMMARY OF THE INVENTION

An object of the invention is to provide a medical instrument which can be used exclusively as a simple forceps or as a bipolar coagulation instrument and wherein the conversion can be effected practically instantaneously whenever the need arises.

Another object of the invention is to provide a novel and improved device which can be used to connect a forceps with a source of electrical energy.

A further object of the invention is to provide a medical instrument which is constructed in such a way that the cable which is used to connect the electrodes of the forceps with a source of high-frequency electrical energy is not in the way when the forceps is used solely as a means for preparing the tissue and/or vessels for coagulation.

An additional object of the invention is to provide an instrument of the above outlined character which can employ slightly modified versions of conventional forcipes.

Still another object of the invention is to provide a novel and improved method of selectively connecting or disconnecting a coagulation forceps to and from a source of electrical energy.

Another object of the invention is to provide a bipolar medical coagulation instrument whose versatility greatly exceeds those of heretofore known medical instruments.

An additional object of the invention is to provide a medical instrument whose forceps can be used for coagulation purposes even if the orientation of the cable which connects it to a source of electrical energy is or must be changed within a wide range.

A further object of the invention is to provide an instrument which enables a surgeon to manipulate the forceps while the latter is being converted from a strictly mechanical to a coagulation instrument or vice versa.

The invention is embodied in a bipolar medical instrument which comprises a forceps having two elongated legs each of which constitutes a coagulation electrode having a jaw and a first terminal which is remote from the jaw. The jaws of the two legs are movable toward and away from each other, and the forceps further comprises a first electrically insulating carrier which maintains the terminals at a fixed distance from each other. The medical instrument further comprises a substantially pistol-shaped coupling device which serves to connect the first terminals with a source of electrical energy and includes a pair of conductors having second terminals, and a second insulating carrier for the second terminals. The coupling device is movable by hand to and from at least one position in which each second terminal merely abuts one of the first terminals so that the forceps can be used as a bipolar coagulation instrument as long as the second terminals abut the respective first terminals, i.e., it is not necessary to place the second terminals into a frictional, force-locking or form-locking engagement with the first terminals.

The first carrier comprises a first portion between the first terminals and a second portion which is disposed between the legs intermediate the first portion and the jaws. Such first and second portions of the first carrier are or can be integral with one another.

In accordance with a presently preferred embodiment of the invention, one of the insulating carriers (preferably the second carrier) defines a socket for the respective (second) terminals, and the (first) terminals which are insulated from each other by the other (first) carrier extend into the socket in the one position of the coupling device. The one carrier has an internal surface which surrounds the socket and has a substantially circular cross-sectional outline (this can be achieved by imparting to the internal surface a conical shape). The terminals which are insulated from each other by the one carrier preferably extend into the socket (i.e., inwardly beyond the internal surface of the one carrier), and the terminals which are insulated from each other by the other carrier preferably form a composite projection having a substantially circular outline (the projection can have a conical (preferably frustoconical) or can include a spherical portion).

The other carrier can include a substantially flat insulating portion (such as the aforementioned first portion of the first carrier) which is disposed between the respective terminals, and these terminals are preferably mirror symmetrical to each other with reference to the plane of the flat insulating portion.

If the socket of the one carrier is bounded by a conical surface, the maximum-diameter end of such surface is located at or close to the open end of the socket. The terminals which are insulated from each other by the one carrier are preferably disposed opposite each other with reference to the axis of the conical internal surface. The projection formed by the terminals which are insulated from one another by the other carrier preferably includes a substantially cylindrical neck portion which connects a preferably spherical portion of the projection with the intermediate portions of the legs of the forceps. The spherical portion of the projection can enter the socket so that the corresponding parts of the terminals which form the projection can contact the terminals in the socket. The neck portion renders it possible to swivel the second carrier through a relatively large angle while the second terminals abut the first terminals.

The jaws preferably constitute first end portions and the first terminals preferably constitute second end portions of the respective legs. Each first terminal can constitute approximately one-half of the aforementioned projection.

The first terminals can constitute extensions of the elongated intermediate portions of the respective legs. The width of each second terminal (each such terminal can constitute a flat prong) is preferably less than or does not exceed the thickness of the aforementioned flat insulating portion of the first carrier intermediate the first terminals. This reduces the likelihood of the establishment of contact between one first terminal and both second terminals or vice versa.

The second carrier can resemble a dog's leg, i.e., it can have two mutually inclined sections. The second terminals are preferably disposed at the free end of one such section and the conductors extend from the free end of the other section. The coupling device preferably further comprises an electric switch which is installed in one of the conductors to open or complete the circuit including the electrodes and the second terminals in the one position of the second carrier. Portions of conductors are preferably embedded in the second carrier.

The novel features which are considered as characteristic of the invention are set forth in particular in the appended claims. The improved bipolar medical instrument itself, however, both as to its construction and the mode of manipulating the same, together with additional features and advantages thereof, will be best understood upon perusal of the following detailed description of certain specific embodiments with reference to the accompanying drawing.

BRIEF DESCRIPTION OF THE DRAWING

FIG. 1 is a schematic partly elevational and partly sectional view of a bipolar medical instrument which embodies one form of the invention, the carrier of the coupling device being spaced apart from the spherical portion of the projection which is formed by the terminals of the legs forming part of the forceps;

FIG. 2 is an enlarged view of a detail in the medical instrument of FIG. 1, the first terminals and the adjacent intermediate portions of the legs of the forceps being shown in a longitudinal sectional view and that position of the projection in which the latter extends into the socket of the second carrier being indicated by broken lines;

FIG. 3 is a similar enlarged view of a detail in a modified medical instrument wherein the first terminals together form a frustoconical projection;

DESCRIPTION OF THE PREFERRED EMBODIMENTS

Figure 4:
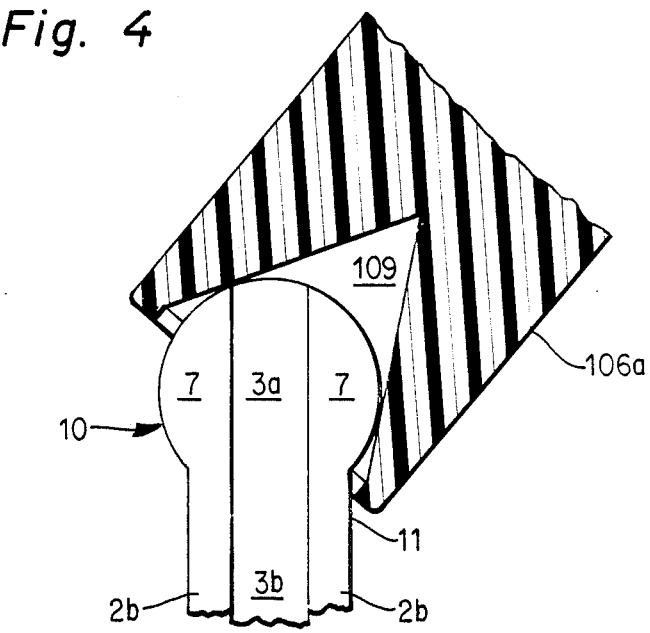
FIG. 4 is an enlarged view of a detail in a third medical instrument wherein the second carrier defines a conical socket for a spherical portion of the projection which is formed by the first terminals.

The bipolar medical instrument which is shown in FIGS. 1 and 2 comprises a forceps 1 and a coupling device 6. The forceps 1 comprises two elongated legs 2 each of which includes a jaw 2a at one end, a terminal 7 at the other end, and an elongated intermediate portion 2b between the jaw 2a and the terminal 7. Each of the terminals 7 preferably constitutes a rearward extension of the respective intermediate portion 2b. Each jaw 2 constitutes a coagulation electrode and the forceps 1 further includes an electrically insulating carrier 3 having a sleeve-like part 4 which surrounds the intermediate portions 2b of the legs 2 adjacent to the terminals 7, a flat portion 3a which is disposed between the terminals 7, and a further flat portion 3b which extends between the intermediate portions 2b adjacent to the terminals 7 and is integral with the sleeve-like part 4 as well as with the flat portion 3a. The carrier 3 maintains the terminals 7 and the intermediate portions 2b of the legs 2 out of contact with one another. The manner in which the carrier 3 is applied to the rear ends of the legs 2 can be similar to or identical with that disclosed in commonly owned German Pat. No. 30 12 849.

The terminals 7 together form a projection having a spherical portion 10 and a smaller-diameter cylindrical portion 11 which latter connects the spherical portion 10 with the adjacent ends of the intermediate portions 2b of the legs 2. The diameter of the cylindrical portion 11 can be a fraction (e.g., one-third) of the diameter of the spherical portion 10.

The coupling device 6 comprises two electrical conductors 14 and a second carrier 6a which consists of an electrically insulating material and resembles a dog's leg having a first section 6a' and a second section 6a". The free end of the section 6a' is formed with a socket 9 which is bounded by a frustoconical internal surface 9a, and the conductors 14 have terminals 8 which are located in the socket 9 and are disposed opposite each other with reference to the axis of the internal surface 9a. The terminals 8 are preferably flat strip-shaped prongs which are resilient and normally tend to extend into the socket 9 (see FIG. 1). The conductors 14 have bare portions which are embedded in the insulating material of the carrier 6a and these conductors extend into an insulating sheath 5 at the free end of the section 6a" of the carrier 6a. Those ends of the conductors 14 which are remote from the coupling device 6 are connected or connectable to a source of high-frequency electrical energy, not shown.

The maximum-diameter end of the internal surface 9a is disposed at the open end of the socket 9. This renders it possible to readily introduce the spherical portion 10 of the projection at the rear end of the forceps 1 into the socket 9 so that each of the terminals 7 merely abuts one of the terminals 8. The coagulating operation can proceed as soon as the surgeon or another person completes the circuit including the legs 2 and the terminals 8 by closing an electric switch 13 whose mobile part extends from the carrier 6a in the region where the sections 6a' and 6a" merge into each other. The forceps 1 can be inserted into an animal cavity in a first step, and the carrier 6a is then manipulated by hand so as to place the terminals 8 into abutment with the terminals 7 preparatory to closing of the switch 13 which is installed in one of the conductors 14. The relative positions of the forceps 1 and coupling device 6 when each terminal 8 contacts one of the terminals 7 are respectively shown in FIG. 2 by broken and solid lines. It will be seen that the circuit of the electrodes including the legs 2 can be completed without the establishment of a frictional, force-locking or form-locking connection between the carriers 3, 6a and the two pairs of terminals 7 and 8, i.e., it is not necessary that the spherical portion 10 of the projection be held in the socket 9 by snap action, by detent means or in any other positive or halfway positive manner. This renders it possible to use the forceps 1 independently of the carrier 6a in a conventional manner in general surgery or orthopedics and to shift to bipolar coagulation whenever desired or necessary by the simple expedient of manipulating the coupling device 6 so as to place each of the terminals 8 into abutment with one of the terminals 7.

Figure 5:
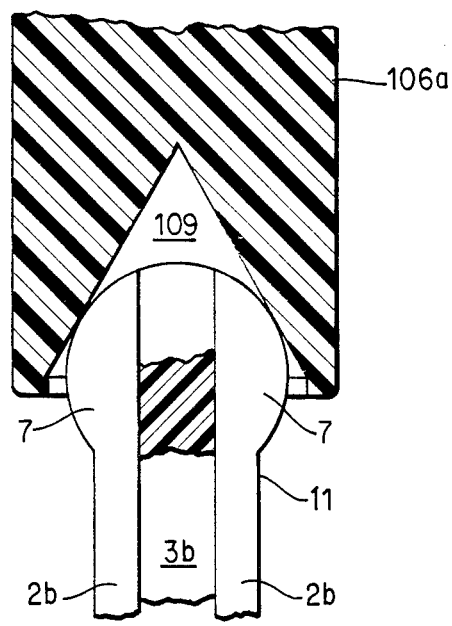
FIG. 5 shows the structure of FIG. 4 but with the second carrier in a different orientation relative to the projection.

It will be seen that the projection at the rear ends of the legs 2 has a circular cross-sectional outline (in each of a number of planes which are normal to the axis of the cylindrical portion 11), and the same applies for the surface 9a which surrounds the socket 9. The flat portion 3a of the insulating carrier 3 is located in the plane including the axis of the cylindrical portion 11 of the projection, and the halves of the spherical portion 10 are mirror symmetrical to each other with reference to such plane. Each of the terminals 7 forms substantially one-half of the cylindrical portion 11 as well as substantially one-half of the spherical portion 10. The provision of a projection which includes a spherical portion 10 and a smaller-diameter cylindrical portion 11 exhibits the advantages which can be appreciated by looking at FIGS. 4 and 5 showing a slightly modified carrier 106a having a conical socket 109. The conductors 14 are not specifically shown in FIGS. 4 and 5. It will be seen that the carrier 106a can swivel relative to the spherical portion 10 within a large angle while the terminals 7 remain in adequate conductive contact with the terminals of the conductors. While it is also possible to provide the socket at the rear end of the forceps 1 and to provide the conductors 14 with terminals which constitute or form part of a spherical or conical projection, the construction which is shown in the drawings is preferred at this time. The socket 9 or 109 can be moved to a position in which each terminal 8 abuts against one of the terminals 7 while the axis of the internal surface surrounding the socket coincides with the axis of the cylindrical portion 11 of the projection (FIG. 5) or while such axes make a relatively small or even a very large acute angle (FIG. 4). The relationship between the diameters of the portions 10 and 11 can be such that the carrier 6a or 106a can swivel from the position of FIG. 5 to all sides within an angle of up to and even in excess of 40 degrees.

The width of each of the terminals 8 is preferably selected in such a way that it at most equals but can be less or much less than the thickness of the exposed part of the flat insulating portion 3a between the terminals 7 of the legs 2. This greatly reduces the likelihood of moving the coupling device 6 to a position in which one terminal 8 contacts both terminals 7 or vice versa, i.e., such selection of dimensions of the terminals 8 reduces the likelihood of short-circuiting the electrodes which are constituted by the legs 2 of the forceps 1. Thus, all that can happen is that the circuit including the terminals 7 and 8 is interrupted, i.e., that the coagulation is interrupted. The surgeon or even an assistant then merely changes the inclination and/or angular position of the coupling device 6 with reference to the forceps 1 in order to complete the circuit and to resume the coagulation process.

The utilization of a carrier 6a or 106a which resembles a dog's leg is preferred at this time because it enables a person who manipulates the coupling device 6 to stand at one side of the person manipulating the forceps 1 and to move the terminals 8 into or from abutment with the terminals 7. The carrier 6a or 106a insulates all bare portions of the conductors 14 and confines the terminals 8 in the socket 9 or 109 so as to ensure danger-free manipulation of the medical instrument.

The construction of the coupling device including the carrier 6a of FIG. 3 is or can be identical with that of the coupling device which is shown in FIGS. 1 and 2. The terminals 207 at the rear ends of the legs 202 together form a frustoconical projection 210 which can be received in the socket 9. The versatility of the medical instrument of FIG. 3 is somewhat less pronounced because the carrier 6a cannot swivel within an angle which is as large as that shown in FIG. 4. The first carrier (including the flat insulating portion 3b shown in FIG. 3) can be identical with the carrier 3 of FIG. 1.

The improved medical instrument exhibits the advantage that the forceps 1 can be used independently of the coupling device 6 and that the electrodes or legs of such forceps can be connected with or detached from an energy source practically instantaneously and without necessitating any, even negligible, shifting of the forceps with reference to the tissue or vessels which are clamped by the jaws 2a. This renders it possible to employ the forceps in the customary way as well as for bipolar coagulation as frequently as desired and at regular or irregular intervals, and also for the surgeon to continue to employ and manipulate the forceps while the terminals 7 or 207 are being connected to or detached from the terminals 8. Thus, the sheath 5 does not interfere with the manipulation of the forceps 1 when the latter is used as a conventional clamping, gripping or holding instrument, and the sheath interferes little (if at all) with the manipulation of the forceps 1 when the latter is used as a component of a bipolar medical instrument because the coupling device 6 can be moved to any one of a practically infinite number of different positions with reference to the insulating carrier 3 at the rear ends of the legs 2 or 202.

The absence of any positive or substantially positive connection between the terminals 8 and 7 (i.e., the absence of frictional, clamping or like engagement between such terminals) renders it possible to establish and terminate the connection between the coagulation electrodes (legs) 2 or 202 of the forceps 1 and the energy source without any delay as soon as and as long as the need arises. This is in contrast to the teaching of the aforediscussed German Pat. No. 30 12 849 which discloses a bipolar coagulation forceps with a positive connection between the plug at the rear end of the forceps and the receptacle at one end of a cable whose other end is attached to a source of high-frequency electrical energy. As mentioned above, the forceps 1 can be manipulated by a surgeon while an assistant manipulates the coupling device 6 to establish or interrupt a connection between the terminals 7 or 207 and the energy source. Were the mere abutment of terminals 8 and 7 or 207 replaced with a more positive connection (e.g., a frictional engagement between such parts), it would be very difficult or plain impossible to hold the forceps 1 against any movements relative to the body of a patient while the terminals 8 are in the process of moving into or out of contact with the terminals 7 or 207. The provision of the socket 9 or 109 and projection 10 or 210 renders it possible to ensure even more rapid and predictable establishment of contact between the terminals 7 or 207 and 8. The surface 9a or 109a guides the projection during movement of terminals 8 toward or away from engagement with the corresponding terminals 7 or 207. A small angular displacement of the carrier 6a or 106a relative to the terminals 7 or 207 suffices to establish a satisfactory current-conducting connection between the terminals 7 or 207 and 8 if the initial engagement between the projection and the surface 9a or 109a failed to result in immediate establishment of an electrical connection between each of the jaws 2a and one of the terminals 8. All the person grasping the coupling device 6 has to do is to exert a minimal pressure in a direction toward the rear end of the forceps 1 to thereby ensure that the terminals 8 are held in contact with the terminals 7 or 207 as long as is necessary to complete the coagulating step.

The aforediscussed selection of the width of the terminals 8 (with reference to the thickness of the portion 3a of the carrier 3) ensures that the coupling device 6 is highly unlikely to hold the carrier 6a or 106a in such orientation that each of the terminals 8 would fail to contact a discrete terminal 7 or 207, or that a terminal 8 would contact both terminals 7 or 207 (or vice versa). Moreover, if such situation would develop, a minute angular displacement of the internal surface 9a or 109a suffices to establish the desirable electrical connection between the terminals 7 or 207 and the energy source.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A bipolar medical instrument, comprising a forceps having two elongated legs each of which constitutes a coagulation electrode having a jaw and a first terminal remote from the jaw, said jaws being movable toward and away from each other and said forceps further comprising a first insulating carrier which insulates said terminals from each other; and a coupling device for connecting said first terminals with a source of electrical energy, including a pair of conductors having second terminals and a second insulating carrier which insulates said second terminals from one another, said device being movable with reference to said forceps by hand to and from at least one position in which each of said second terminals abuts one of said first terminals as long as said device continues to be held by hand in said at least one position so that the forceps can be used as a bipolar coagulation instrument only as long as said second terminals abut the respective first terminals because said device is held by hand in said at least one position, one of said insulating carriers defining a socket for the respective terminals and the terminals which are insulated from each other by the other of said carriers extending into said socket in said at least one position of said device, said one carrier having a surface surrounding said socket and having an at least substantially circular cross-sectional outline.

2. The medical instrument of claim 1, wherein said first carrier comprises a first portion between said first terminals and a second portion disposed between said legs intermediate said first portion and said jaws.

3. The medical instrument of claim 2, wherein the first and second portions of said first carrier are integral with each other.

4. The medical instrument of claim 1, wherein the terminals which are insulated from each other by said one carrier extend into said socket.

5. The medical instrument of claim 1, wherein the terminals which are insulated from each other by said other carrier together form a composite projection having a substantially circular cross-sectional outline.

6. The medical instrument of claim 5, wherein said other carrier includes a substantially flat insulating portion which is disposed between the respective terminals and such terminals are substantially mirror symmetrical to each other with reference to the plane of said insulating portion.

7. The medical instrument of claim 1, wherein said socket has an open end and said one carrier has a substantially conical internal surface surrounding said socket and having a maximum diameter in the region of said open end.

8. The medical instrument of claim 7, wherein the terminals which are insulated from each other by said one carrier extend from said internal surface and into said socket, such terminals being disposed opposite each other with reference to the axis of said conical surface.

9. The medical instrument of claim 1, wherein the terminals which are insulated from each other by said other carrier together constitute a substantially conical projection.

10. The medical instrument of claim 9, wherein said projection constitutes the frustum of a cone.

11. The medical instrument of claim 1 wherein the terminals which are insulated from each other by said other carrier together constitute a projection having a substantially spherical portion receivable in said socket.

12. The medical instrument of claim 11, each of said legs having an intermediate portion between the respective jaw and first terminal; and wherein said projection further includes a substantially cylindrical neck portion which connects said spherical portion with the intermediate portions of said legs.

13. The medical instrument of claim 1, wherein said socket is provided in said second carrier and said first terminals constitute a projection which is insertable into and withdrawable from said socket.

14. The medical instrument of claim 13, wherein said jaws constitute first and said first terminals constitute second end portions of the respective legs.

15. The medical instrument of claim 13, wherein each of said first terminals constitutes approximately one-half of said projection.

16. The medical instrument of claim 1, wherein each of said legs further comprises an elongated intermediate portion and each of said first terminals constitutes an extension of the respective intermediate portion.

17. The medical instrument of claim 1, wherein said other carrier includes a substantially flat insulating portion having a predetermined thickness and being disposed between the respective terminals, the terminals in said one carrier being disposed in said socket opposite each other and each thereof having a width which at most equals said predetermined thickness.

18. The medical instrument of claim 1, wherein said second carrier includes two mutually inclined sections each of which has a free end, said second terminals being disposed at the free end of one of said sections and said conductors extending from said second carrier at the free end of the other of said sections.

19. The medical instrument of claim 1, wherein said device further comprises an electrical switch which is installed in one of said conductors to open or complete the circuit including said electrodes and said second terminals in said at least one position of said second carrier.

20. The medical instrument of claim 1, wherein said conductors have portions which are embedded in said second carrier.

21. The medical instrument of claim 1, wherein the terminals which are insulated from each other by said other carrier together form a composite projection having a substantially circular cross-sectional outline, said projection being receivable in said socket.

22. The medical instrument of claim 4, said socket having an axis; and wherein the terminals which are insulated from each other by said one carrier are disposed opposite each other with reference to said axis.

23. The medical instrument of claim 1, wherein the terminals which are insulated from each other by said one carrier are resilient.

* * * * *